(12) United States Patent
Kuenzi et al.

(10) Patent No.: US 12,708,689 B2
(45) Date of Patent: Aug. 18, 2026

(54) SYSTEM AND METHOD FOR DETERMINING SANITIZATION STATUS

(71) Applicant: HONEYWELL INTERNATIONAL INC., Charlotte, NC (US)

(72) Inventors: Adam Kuenzi, Palm Beach Gardens, FL (US); Subhash Reddy Gopavaram, Hyderabad (IN); Mohan Reddy Dumbala, Hyderabad (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 694 days.

(21) Appl. No.: 18/175,579

(22) Filed: Feb. 28, 2023

(65) Prior Publication Data

US 2023/0277707 A1 Sep. 7, 2023

(30) Foreign Application Priority Data

Mar. 2, 2022 (IN) ............................ 202211011265

(51) Int. Cl.

| | |
|---|---|
| ***A61L 2/28*** | (2006.01) |
| ***A61L 2/24*** | (2006.01) |
| ***A61L 103/75*** | (2026.01) |
| ***G07C 9/00*** | (2020.01) |
| ***G07C 9/22*** | (2020.01) |

(52) U.S. Cl.

CPC .................................... *A61L 2/28* (2013.01); *A61L 2/24* (2013.01); *G07C 9/00309* (2013.01); *G07C 9/00904* (2013.01); *G07C 9/22* (2020.01); *A61L 2103/75* (2026.01); *A61L 2202/14* (2013.01); *G07C 2009/00769* (2013.01); *G07C 2209/08* (2013.01); *G07C 2209/62* (2013.01)

(58) Field of Classification Search

None

See application file for complete search history.

(56) References Cited

U.S. PATENT DOCUMENTS

| | | | | |
|---|---|---|---|---|
| 10,369,242 | B1 | 8/2019 | Kellogg, Jr. | |
| 2017/0173200 | A1 | 6/2017 | Wyman et al. | |
| 2020/0397936 | A1 | 12/2020 | Deros et al. | |
| 2021/0257085 | A1 * | 8/2021 | Arumugam ............ | G16H 40/20 |

(Continued)

FOREIGN PATENT DOCUMENTS

| | | | |
|---|---|---|---|
| CN | 105497936 | A | 4/2016 |
| EP | 3795779 | A1 | 3/2021 |

OTHER PUBLICATIONS

European Search Report for Application No. 23159493.8, Issued Feb. 21, 2024, 19 Pages.

*Primary Examiner* — Carlos Garcia

(74) *Attorney, Agent, or Firm* — Seager, Tufte & Wickhem, LLP

(57) ABSTRACT

Configuring a sanitization mode for a predetermined time interval for sanitizing a premises. A first predefined pattern is received on a lock associated with the premises from a user within the predetermined time interval to indicate starting of the sanitization process. Subsequently, a second predefined pattern is received on the lock within the predetermined time interval to indicate a completion of the sanitization process. An indicator is displayed based on the first predefined pattern and the second determined pattern and simultaneously communicating the sanitization status to an authorized user.

17 Claims, 4 Drawing Sheets

(56) References Cited

U.S. PATENT DOCUMENTS

| | | | |
|---|---|---|---|
| 2021/0308311 | A1 | 10/2021 | Stewart |
| 2022/0005298 | A1 | 1/2022 | Shen |
| 2022/0055449 | A1 | 2/2022 | Van Wiemeersch et al. |

* cited by examiner

SYSTEM AND METHOD FOR DETERMINING SANITIZATION STATUS

FOREIGN PRIORITY

This application claims priority to Indian Patent Application No. 202211011265, filed Mar. 2, 2022, and all the benefits accruing therefrom under 35 U.S.C. § 119, the contents of which in its entirety are herein incorporated by reference.

TECHNICAL FIELD OF INVENTION

The present invention relates to a field of sanitization. More particularly, the present invention relates to the system and method of determining sanitization status of premises.

BACKGROUND OF THE INVENTION

Due to the Covid-19 pandemic, large premises such as hotels, schools, hospitals, restaurants etc. have to operate under strict sanitary restrictions. The premises are required to be sanitized and disinfected to ensure a safe stay for their occupants. Therefore, sanitization of the premises is a major concern amongst the management of such places.

Various measures are taken to prevent the spread of infection amongst the occupants, such as providing hand sanitizer dispensers at various convenient locations, and making it mandatory to wear face masks, at least on the premises. Additional measures such as sanitization of rooms prior to their occupation are also undertaken. However, it is still unknown to the occupant such as a guest in a hotel whether the premises or area used by the him/her is properly sanitized or not. And even if such awareness is there, the guest may still be unsure of whether the sanitization of the premises is properly executed or not.

Sanitization or disinfection of a premises is thus a crucial concern to a user or an occupant also may have questions/doubts about prior sanitization of the room that he/she is going to check-in or occupy.

In view of the afore-mentioned problems in the existing solutions, there is a need of a robust system and a method for altering the sanitization status and indicating to the occupant before he/she enters the premises. Also, there is requirement of a system and a method that can efficiently measure the effectiveness of the sanitization of the premises. There is also a need of a system and method of determining the sanitization status of the premises without manual inspection of the premises. There is a need that the occupant does not have raise any questions/doubts about prior sanitization of the premises. In order to solve the problems in the existing solutions, a system and a method are disclosed.

SUMMARY OF THE INVENTION

Various embodiments of the invention describe a system and a method to identify the sanitization status of inside a premises such as rooms and the like. The method comprises configuring a sanitization mode for a predetermined time interval for sanitizing a premises. The method is further configured to receive a first predefined pattern on a lock from a user within the predetermined time interval to indicate starting of the sanitization process. The method then receives a second predefined pattern on the lock within the predetermined time interval to indicate a completion of a sanitization process and display an indicator based on the first predefined pattern and the second determined pattern to indicate a sanitization status and simultaneously communicating the sanitization status to an authorized user.

In an embodiment of the invention, a mobile device of the authorized person is configured to communicate with the lock of the premises and fetch the sanitization status of the premises.

In an embodiment of the invention, the mobile device of the authorized person uses a client application to communicate with the lock.

In an embodiment of the invention, the first predefined pattern and the second determined pattern are enabled on a virtual lock rendered on a client application of a user device associated with the user.

In yet another embodiment of the invention, the first predefined pattern and the second determined pattern are configured to enable the sanitization status of the premises only within the predetermined time interval.

In still another embodiment of the invention, the sanitization status comprises a count of the first predefined pattern and the second predefined pattern within a predetermined time.

In another embodiment of the invention, the first predefined pattern comprises turning a handle of the lock downwards for a first count and the second predefined pattern comprises turning ON/OFF a dead bolt of the lock for a second count.

In another embodiment of the invention, the premises comprises a sensor configured to sense a level of sanitization inside the premises.

In still another embodiment of the invention, the sensor is configured to compare the level of sanitization with a predefined value.

In an embodiment of the invention, the sensor wirelessly communicates the level sanitization to the lock of the premises.

In still another embodiment of the invention, the authorized user is a guest and on indication that the sanitization process is completed, the lock is only accessible by the guest and restricted to other authorized users.

Various other embodiments of the invention also describe a system comprising a lock associated with a premises and configured with a sanitization mode for a predetermined time interval for sanitizing the premises. The lock is further configured to receive a first predefined pattern on a lock from a user within the predetermined time interval to indicate starting of the sanitization process. The system is further configured to receive a second predefined pattern on the lock within the predetermined time interval to indicate a completion of the sanitization process. The lock is also configured to display an indicator based on the first predefined pattern and the second determined pattern indicating a sanitization status and simultaneously communicate the sanitization status to an authorized user.

In an embodiment of the invention, a mobile device of the authorized person is configured to communicate with the lock of the premises and fetch the sanitization status of the premises.

In an embodiment of the invention, the mobile device of the authorized person uses a client application to communicate with the lock.

In yet another embodiment of the invention, the first predefined pattern and the second determined pattern are configured to enable the sanitization status of the premises only within the predetermined time interval.

In still another embodiment of the invention, the sanitization status comprises a count of the first predefined pattern and the second predefined pattern within a predetermined time.

In another embodiment of the invention, the first predefined pattern comprises turning a handle of the lock downwards for a first count and the second predefined pattern comprises turning ON/OFF a dead bolt of the lock for a second count.

In another embodiment of the invention, the premises comprises a sensor configured to sense a level of sanitization inside the premises.

In still another embodiment of the invention, the sensor is configured to compare the level of sanitization with a predefined value and the sensor wirelessly communicates the level sanitization to the lock of the premises.

In still another embodiment of the invention, the authorized user is a guest and on indication that the sanitization process is completed, the lock is only accessible by the guest and restricted to other authorized users.

Various embodiments of the invention disclose a computer readable medium comprising one or more processors and a memory coupled to the one or more processors, the memory storing instructions executed by the one or more processors. The one or more processors is configured to configure a sanitization mode for a predetermined time interval for sanitizing a premises. The one or more processors is configured to receive a first predefined pattern on a lock from a user within the predetermined time interval to indicate starting of the sanitization process. The one or more processors is further configured to receive a second predefined pattern on the lock within the predetermined time interval to indicate a completion of the sanitization process and display an indicator based on the first predefined pattern and the second determined pattern indicating a sanitization status and simultaneously communicating the sanitization status to an authorized user.

Other aspects, advantages, and salient features of the invention will become apparent to those skilled in the art from the following detailed description, which taken in conjunction with the annexed drawings, discloses exemplary embodiments of the invention.

BRIEF DESCRIPTION OF THE DRAWINGS

Some of the objects of the invention have been set forth above. These and other objects, features, aspects and advantages of the present invention will become better understood with regard to the following description, appended claims and accompanying drawings where:

Corresponding reference numerals indicate corresponding parts throughout the drawings.

DETAILED DESCRIPTION OF THE INVENTION

Embodiments of the invention describe system and method to identify the sanitization status of the premises. Various embodiments of the invention describe a system and a method to indicate sanitization status of a premises such as a room. A sanitization mode is configured for a predetermined time interval for sanitizing the premises. A first predefined pattern is received on a lock associated with the premises from a user within the predetermined time interval to indicate starting of the sanitization process. Further, a second predefined pattern is received on the lock within the predetermined time interval to indicate a completion of the sanitization process. An indicator based on the first predefined pattern and the second determined pattern indicates sanitization status and simultaneously communicates the sanitization status to an authorized user.

As used herein, the premises includes one or more enclosed spaces, for example a home, hotel, apartment, office, hospital, or a room in these places and other types of accommodations that typically accommodate people.

As used herein, the premises may comprise a door comprising a door lock. The door lock may comprise a handle and a dead bolt. The door lock may comprise a sensor configured to sense the movement of the door handle and the dead bolt. The door lock may also comprise an indicator or may be associated with an indicator which may be separate from the door lock. The door lock may comprise a door handle which is installed at a location exterior of the room, i.e., outside the door. For example, in a hotel, the room may be considered as the premises and the door handle of the room may be accessible from hallway side. The dead bolt of the lock may be provided on the door lock accessible from inside the room, i.e. on the opposite side of the handle. Moreover, the dead bolt may also include another handle which may be present along with the dead bolt and accessible from inside the room.

As used herein, the network may refer to a wired network, a mesh network, a cellular network such as Global System for Mobile (GSM) network, a Long-Term Evolution (LTE) network, a code-division multiple access (CDMA) network, a narrow-band internet of thing (NB-IoT) technique or category M1 technique or any such network/technique that is known in the art.

As used herein, the user device such as mobile device may communicate with the door lock and the various devices and terminals within the building using short-range communication like Bluetooth and Wi-Fi.

Figure 1:
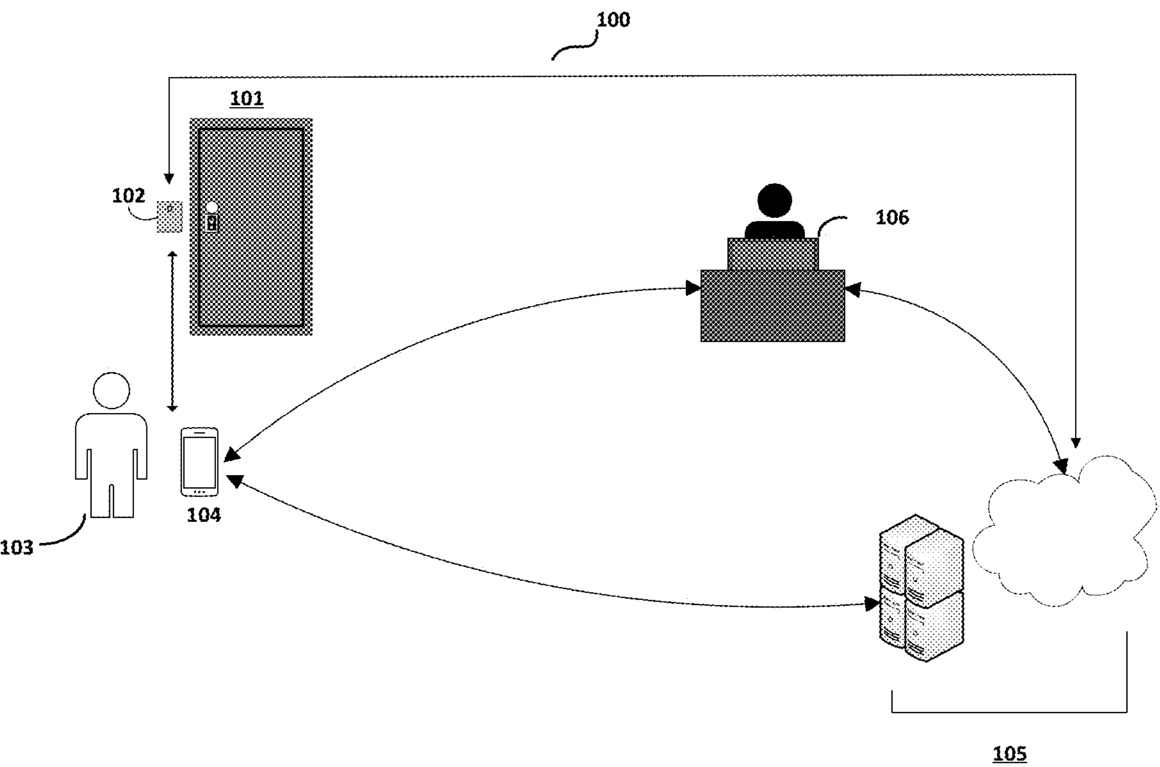
FIG. 1 illustrates an exemplary system according to an exemplary embodiment of the invention.

FIG. 1 illustrates an exemplary embodiment of a system 100. The system 100 comprises a premises with a door 101 which comprises a door lock 102 having a depressible handle, a sensor, and an indicator (not shown). The door lock 102 may be installed on the door with door handle at a location outside the door or on a hallway side of the premises. The door lock 102 may be communicably coupled to a server 105 through a network. An administrator 106 may also be communicably coupled over the network using a terminal. Any authorized user 103 may use a user terminal/mobile device 104 to communicate with the door lock 102 as well as the server 105 over the network. The administrator 106 may configure a sanitization mode for the premises for a predetermined duration of time.

The door lock 102 may have a depressible handle which may be moved from one fixed position to a plurality of other fixed positions within the lock. A user may enter the premises after entering a key which may be a physical key or an electronic key. The key may be read by the lock to authenticate a user accessing the lock. After authentication, the user may perform one or more functions associated with the premises as intended. While using the electronic key, the user 103 may use the user credentials stored on the user terminal 104. The user terminal 104 and the door lock 102 may communicate wirelessly using the electronic door lock. The user credentials may be transmitted from the user terminal 104 over the Bluetooth and the door lock may authenticate the user 103 to enter the room.

Figure 2A:
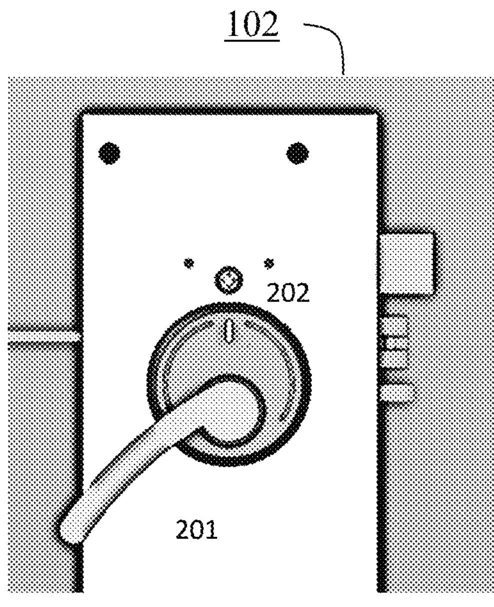
FIGS. 2A and 2B illustrates the door lock according to an exemplary embodiment of the invention.
Figure 2B:
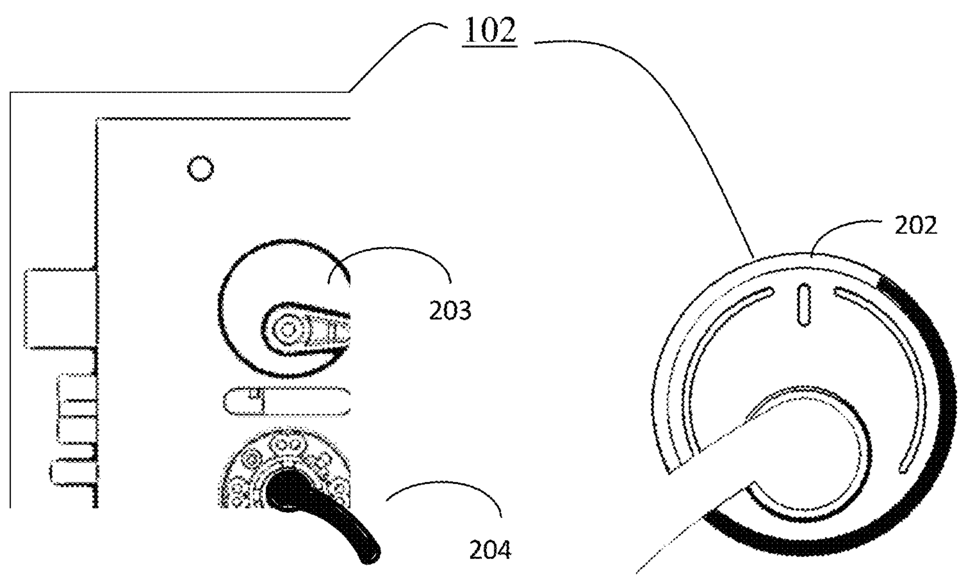

Turning to FIGS. 2A and 2B, where description with regards to the indication of a sanitization status for the premises is described. The door lock 102 comprises a door handle 201 and an indicator 202. The door lock 102 may further comprise a dead bolt 203 located on the door lock 102 on the opposite side of the door handle 201. That is, the dead bolt 203 may be accessible by the user from inside the room. There may also be another handle accessible from inside the room. The user such as a person authorized to clean and sanitize the room may use a user terminal 104 to access the premises using the user credentials as described above. The user credentials may be provided to the user 103 on the user terminal 104 by the administrator 106 using the network as shown in FIG. 1. The user credentials may be provided to the user within the predetermined time interval or at the time of starting the predetermined time interval. The predetermined time interval may be a time duration provided to sanitize the premises by the user 103, for example from 9:00 AM to LOAM on a particular date or every day. The door lock 102 further comprises a sensor (not shown) which is configured to sense a first predefined pattern such as counts of turning operations of depressible handle 201 and second predefined pattern such as count of turning ON and OFF operation of the dead bolt 203 within the predetermined time. The second predefined pattern may include turning operations of another handle 204 from inside the door lock 102. The indicator 202 may be a light emitting diode (LED) or a display configured to display information thereof, regarding the status of the sanitization.

The user 103 after authentication may depress or move the handle 201 from a first fixed position, and then to a second fixed position, and further to a third fixed position and so on to a nth fixed position. The sensor may count the change in positions of the door handle 201 due to the movement of the handle from a first fixed position to a nth (n is a finite number) fixed position which may be represented as the first predefined pattern. The depression of the door handle 201 for the first predefined pattern indicates the start of the sanitization process. The start of the sanitization process may be indicated by a color such as YELLOW on the indicator 202.

After applying the first predefined pattern, the user 103 may enter inside the room and sanitize the room. After sanitizing the room, the user 103 may press the dead bolt 203 for a predefined count which may be represented as the second predefined pattern. The second predefined pattern may be ON/OFF of the dead bolt/turning operation of another handle accessible from inside the room. The application of the second pattern may indicate completion of the sanitization process. The predetermined time interval may end on applying the second predefined pattern. After sanitization is completed, the indicator 202 may glow in GREEN color indicating that the sanitization is satisfactorily completed. In case the sanitization process is not completed, the indicator may glow in RED color. The color of the indicator may be user configurable and any different color known to a person skilled in the art that may be applied for different situations.

In an embodiment of the invention, the user 103 may use a client application on his/her user terminal 104. The user 103 may use the user credentials to open the door as discussed above and the authentication of the user credentials at the door lock may indicate start of the sanitization process. The user terminal 104 may be configured with a client application on the user terminal 104 which is configured to virtually display a lock associated with the physical lock or having same lock ID as the physical lock. The user 103 may input the first predefined pattern and the second predefined pattern virtually on the virtual lock on the client application to indicate starting and ending of the sanitization process and accordingly, indicator on the door lock 102 may reflect the sanitization status as discussed above. It may be noted that the first predefined pattern and the second predefined pattern may be a same pattern.

In another embodiment of the invention, the sanitization process starts automatically and the LED goes YELLOW indicating start of the sanitization process without any providing any first predefined pattern. Then, on leaving, the user 103 may use the client application on the user terminal 104 to indicate the sanitization is now complete and this would turn the LED to GREEN automatically.

Any authorized user such as a guest may visit for a stay in the room. The authorized user may also be a manager of the premises who may ascertain the sanitization status of the room by looking at the GREEN colored indicator as discussed above. Alternatively, the guest or the manager may use a mobile device (associated with the guest or the manager) with a client application installed therein. The client application on the mobile device may communicate with the door lock 102 using a short-range communication such as Bluetooth and retrieve the sanitization status of the room on the mobile device.

In an embodiment of the invention, using the client application on the mobile device, the guest or the manager may ascertain the correct indication on the indicator 202. The present invention provides the advantage that the guest or the administrator does not need to manually inspect the room and may be assured of the sanitization without entering the room.

In an embodiment of the invention, the authorized user such as guest/manager/supervisor may shares sanitization status of room to hotel FDS (front desk system) via wired/wireless network from the client application associated with the mobile device of the authorized user. Accordingly, the sanitization status for each premises/room inside the building may be updated on the server by the FDS.

In an embodiment of the invention, the door lock 102 may be accessible to an authorized user such as the guest of the premises such as hotel premises when the sanitization process is completed. In other words, other authorized users such as managerial staff or cleaning staff of the premises may not be allowed and restricted by the lock outside the sanitization mode or during the predetermined time.

In another embodiment of the invention, after the guest enters the room/premises the GREEN color of the LED changes to RED color indicating that the room has now been used and need to be sanitized later. This may also be indicated using audit records inside the door lock and accordingly, the LED may derive the sanitization status using the audit records.

Figure 3:
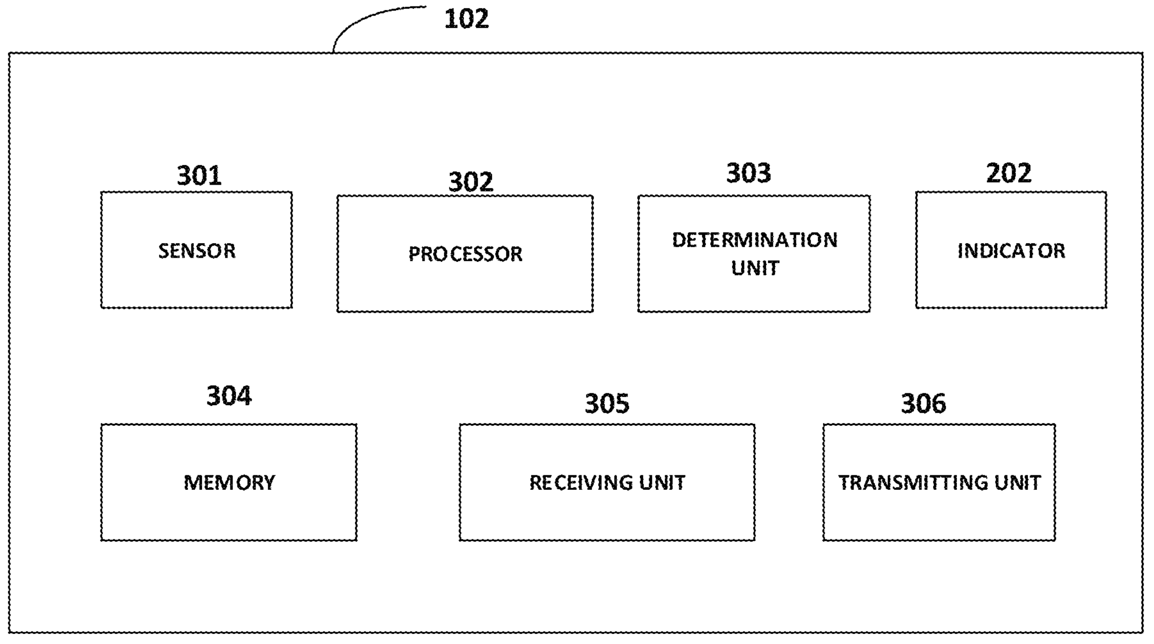
FIG. 3 depicts block diagram of different components of an exemplary door lock according to an exemplary embodiment of the invention

FIG. 3 illustrates various components of the door lock or components associated with the door lock 102. The door lock 102 comprises a sensor 301 as discussed above to sense the first predefined pattern and the second predefined pattern. A processor 302 may be configured to receive the first and second predefined pattern instructions as discussed above from the sensor 301 within a predetermined time. The processor 302 may be configured to use a memory 304 and a determination unit 303 to determine the sanitization status of the room. The processor 302 may be configured to access from the memory information regarding the first predefined pattern and the second predefined pattern and use the determination unit 303 to determine the color for the indicator 202. The processor is further configured to glow the indicator in YELLOW to show that the sanitization process is started. The processor may be further configured to receive the second predefined pattern from the sensor, as discussed above, to set the sanitization status at the lock in GREEN color which indicates that the sanitization process is completed.

The door lock 102 may be configured to transmit the sanitization status/level of sanitization to the server 105 and/or a mobile device of the guest using the transmitting unit 306. The transmitting unit 306 may relay the sanitization status/level of sanitization through the network.

In another embodiment of the invention, there may be one or more second sensors inside the room configured to determine the level of sanitization inside the room after sanitization is completed. The one or more second sensors may be MQ3 sensors which may be installed on the walls or ceilings or any appropriate space within the room. The one or more second sensors may detect contents (e.g., alcoholic content) that may be present in sanitization substances and are likely to be released and emitted into the air during sanitization process. The one or more second sensors may determine the amount of content(s) which may represent the level of sanitization. The one or more second sensors may be configured to wirelessly couple with the door lock 102 and transmit the level of sanitization to a receiving unit 305. The receiving unit 305 may receive the level of sanitization and allow a memory 304 to store the amount of content (in the form of numeric values) determined by the one or more second sensors. The processor 302 may be configured to determine the level of sanitization using the memory 304 and the determination unit 303. The processor 302 may then configure the level of sanitization on the indicator or display 202.

In particular, on receiving the level of sanitization from the one or more second sensors, the processor 302 may be configured to compare the level of sanitization with a threshold level. The processor 302 may be accordingly configured to render the level of sanitization of the indicator 202 using different colors depending upon the level of sanitization in the room. As an example, if the level of sanitization is above the threshold, then a GREEN color indication may be provided on the indicator 202 by the processor 302. Moreover, if the level of sanitization is below the threshold, a RED color may be indicated on the indicator 202. There may be other discrete levels of sanitization which may be represented with corresponding different colors which are also within the scope of the invention. Moreover, the method of processing the level of sanitization by the processor 302 using the memory 304 and the determination unit 303 is also known to a person skilled in the art.

The sensor 301, the determination unit 303, the indicator 202, the memory 304, the receiving unit 305, and the transmitting unit 306 may be communicably coupled with the processor 302. The different units described herein are exemplary. The invention may be performed using one or more units. For example, the tasks executed by the sensor 301, the determination unit 303, the indicator 202, the memory 304, the receiving unit 305, and the transmitting unit 306 may be performed by a single unit. Alternatively, another number of units as described herein may be used to perform the present invention.

As discussed above, a guest may check the sanitization status as well as the level of sanitization with the door lock 102. The guest may use the mobile device to communicate with the processor 302 and the processor may extract the sanitization status and/or the level of sanitization and the values thereof to the guest. Accordingly, the invention provides satisfaction to the guest whether the room has been sanitized to the satisfaction of the guest.

In accordance with another embodiment of the invention, the door lock 102 may be further associated with the guest ID via a client application hosted on the mobile device of the guest. The sanitization status and/or the level of sanitization of the room may be communicated on the mobile device of the guest using the guest ID. Alternatively, the door lock 102 may be configured to transmit the sanitization status and/or the level of sanitization to a server 105 over the network. The server 105 may then transmit the sanitization status and/or the level of sanitization using the guest ID. The identity of the guest can be stored in a database or other data structure with a logical relationship (e.g., via security key, guest ID) within the sever 105. That is, using the guest ID, associated device of the guest may be configured to receive the sanitization status such as starting of sanitization, sanitization in progress, end of the sanitization process in the form of notification, email, SMS, and the like. The sanitization status may also provide with the sanitization related content (for e.g., alcoholic content) inside the room as discussed above.

The present invention is herewith presented using an exemplary situation. In the example, the identification of the sanitization status of the hotel room is discussed. Current sanitization status of the rooms in the hotel may be available with the server. An administrator 106 may determine the rooms to be sanitized based on the condition whether the guest would be checking-in during the day. The administrator may assign a predetermined time interval for each room for sanitization and initiate a sanitization mode. Moreover, the administrator may also assign a user (cleaning person) for each room. Subsequently, the administrator may transmit a notification to each cleaning person to sanitize a corresponding room. The determination of the rooms to be sanitized, configuring the sanitization mode, and assigning a cleaning person (by transmitting user credentials thereof) may be automatically configured by the server 105.

As a result of receiving the notification, the cleaning person arrives at a hotel room at the predetermined time interval say in between 9 am to 10 am i.e., when the sanitization mode is configured for the corresponding room. The cleaning person may authenticate himself/herself using the user credentials as discussed above. Sanitization start indication is determined by the door lock when the cleaning person depresses the lock handle 102 three times. Depressing the lock three times enables a LED 202 affixed with the door to blink or emit a light in YELLOW color light. The door lock 102 is equipped with the sensor 301 and the processor 302. The sensor 301 senses the counts of depressing operation of the handle and the processor 302 executes the count instruction received from the sensor and further enables the LED to blink or emit the YELLOW color light. The YELLOW color informs the passersby or the outsiders that the sanitization process is going on in the room. On completion of the sanitization process, the cleaning person turns OFF and ON the dead bolt 203 installed at the door so that the LED would blink with a different color such as a GREEN color light. The GREEN color light indicates that the room is completely sanitized. The door lock 102 is further configured to transmit the sanitization status to the server 105 of the hotel. The door lock 102 is also configured to transmit the sanitization status to the guest corresponding to the room using guest ID as discussed above. The guest may also use the user application on his mobile device to retrieve the sanitization status from the door lock 102 by communicating with the door lock using short-range communication as discussed above.

In an embodiment of the invention, the guest may configure the user application such as "Do not let me inside the room if not sanitized." Accordingly, when the user is about to enter the room the user application may automatically connect with the door lock using the short-range communication and alert the guest about the sanitization status of the room using a notification, message, buzzer, blinking display and the like.

In another embodiment of the invention, the hotel staff may be inhibited from entering the room of the guest outside the duration of the predetermined time interval or outside the sanitization mode. In other words, even the correct user credentials entered by the hotel staff may deny the entry of the hotel staff inside the room. The invention provides the benefit that outside the sanitization mode only the guest may enter the room and there are less chances that the room may be infected.

In an embodiment of the invention, the sanitization mode may be set each day during the stay of the guest depending upon the authorization by the guest. The server or administrator may provide the option to the guest for timings of sanitization of the room during the stay of the guest.

Figure 4:
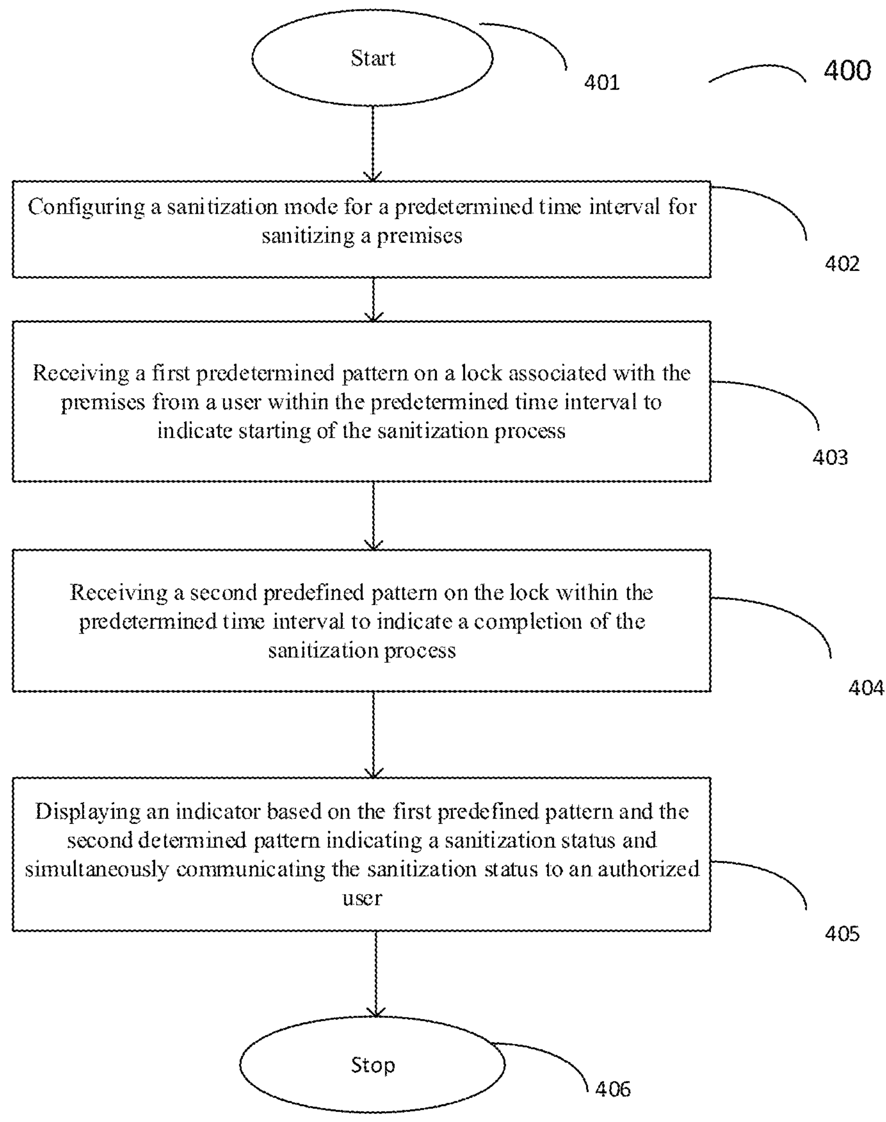
FIG. 4 depicts an exemplary flowchart illustrating a method to perform the invention according to an exemplary embodiment of the invention.

FIG. 4 illustrates an exemplary flowchart illustrating a method to perform the invention according to an exemplary embodiment of the invention. The method flowchart 400 relates to a method of identification of the sanitization status of a premises such as a hotel room. The method flowchart 400 starts at step 401.

At step 402, method describes configuration of sanitization mode for a predetermined time interval for sanitizing a premises. The predetermined time interval is configured as a duration to sanitize the premises which has been discussed with respect to FIGS. 1-3.

At step 403, the method receives a first predefined pattern on a lock associated with the premises by a user within the predetermined time interval to indicate starting of the sanitization process. This has been discussed in detail with respect to FIGS. 1-3.

At step 404, the method receives a second predefined pattern on the lock within the predetermined time interval to indicate a completion of the sanitization process. This has been discussed in detail with respect to FIGS. 1-3.

At step 405, the method displays an indicator based on the first predefined pattern and the second determined pattern and simultaneously communicating the sanitization status to an authorized user. This has been discussed in detail with respect to FIGS. 1-3.

Then, the method may end at step 406.

The embodiments of the invention discussed herein are exemplary and various modification and alterations to a person skilled in the art are within the scope of the invention. The present invention is applicable in any industry/field that is well known in the art for example, in buildings and various places where occupants reside and where the system and method of the present invention may be utilized.

Various embodiments of the present invention describe a computer readable medium configured to perform the operations performed by the present invention. The computer readable medium comprises one or more processors and a memory coupled to the one or more processors. The memory stores instructions executed by the one or more processors. The one or more processors operates to configure a sanitization mode for a predetermined time interval for sanitizing a premises. The one or more processors operates to receive a first predefined pattern on a lock associated with the premises from a user within the predetermined time interval to indicate starting of the sanitization process. The one or more processors further operate to receive a second predefined pattern on the lock within the predetermined time interval to indicate a completion of the sanitization process and display an indicator based on the first predefined pattern and the second determined pattern and simultaneously communicating the sanitization status to an authorized user. The features of the invention as executed and performed by the computer readable medium are discussed in detail with respect to FIG. 1.

Exemplary computer readable media includes flash memory drives, digital versatile discs (DVDs), compact discs (CDs), floppy disks, and tape cassettes. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Computer storage media are tangible and mutually exclusive to communication media. Computer storage media are implemented in hardware and exclude carrier waves and propagated signals. Computer storage media for purposes of this invention are not signals per se. Exemplary computer storage media include hard disks, flash drives, and other solid-state memory. In contrast, communication media typically embody computer readable instructions, data structures, program modules, or other data in a modulated data signal such as a carrier wave or other transport mechanism and include any information delivery media.

Although described in connection with an exemplary computing system environment, examples of the invention are capable of implementation with numerous other general purposes or special purpose computing system environments, configurations, or devices.

Examples of the invention may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the Figures/Tables and described herein. Other examples of the invention may include different computer-executable instructions or components having more or less functionality than illustrated and described herein. Aspects of the invention transform a general-purpose computer into a special-purpose computing device when configured to execute the instructions described herein.

The order of execution or performance of the operations in examples of the invention illustrated and described herein is not essential, unless otherwise specified. That is, the operations may be performed in any order, unless otherwise specified, and examples of the invention may include additional or fewer operations than those disclosed herein. For example, it is contemplated that executing or performing a particular operation before, contemporaneously with, or after another operation is within the scope of aspects of the invention.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," "data storage," "database," "cache," and substantially any other information storage component relevant to operation and functionality of a component, refer to "memory components," or entities embodied in a "memory" or components comprising the memory. It will be appreciated that the memory components, or computer-readable storage media, described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

When introducing elements of aspects of the invention or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of" The phrase "one or more of the following: A, B, and C" means "at least one of A and/or at least one of B and/or at least one of C".

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A method comprising:

configuring a sanitization mode for a predetermined time interval for sanitizing a premises;

receiving a first predefined pattern on a lock associated with the premises from a user within the predetermined time interval to indicate starting of the sanitization process, by sensing turning of a handle of the lock for a count;

receiving a second predefined pattern on the lock within the predetermined time interval to indicate a completion of the sanitization process, by sensing turning of a deadbolt of the lock ON or OFF for a count; and displaying an indicator based on the first predefined pattern and the second predefined pattern indicating a sanitization status and simultaneously communicating the sanitization status to an authorized user.

2. The method as claimed is claim 1, wherein a mobile device of the authorized person is configured to communicate with the lock of the premises and fetch the sanitization status of the premises.

3. The method as claimed in claim 2, wherein the mobile device of the authorized person uses a client application to communicate with the lock.

4. The method as claimed in claim 1, wherein the first predefined pattern and the second predefined pattern are configured to enable the sanitization status of the premises only within the predetermined time interval.

5. The method as claimed in claim 1, wherein the premises comprises a sensor configured to sense a level of sanitization inside the premises.

6. The method as claimed in claim 1, wherein the sensor is configured to compare the level of sanitization with a predefined value.

7. The method as claimed in claim 5, wherein the sensor wirelessly communicates the level sanitization to the lock of the premises.

8. The method as claimed in claim 1, wherein the authorized user is a guest.

9. The method as claimed in claim 1, wherein on indication that the sanitization process is completed, the lock is only accessible by the guest and restricted to other authorized users.

10. A system comprising:

a lock associated with a premises and configured with a sanitization mode for a predetermined time interval for sanitizing the premises, the lock further configured to:

receive a first predefined pattern on the lock associated with the premises from a user within the predetermined time interval to indicate starting of the sanitization process by sensing turning of a handle of the lock for a count;

receive a second predefined pattern on the lock within the predetermined time interval to indicate a completion of the sanitization process, by sensing turning of a deadbolt of the lock ON or OFF for a count; and display an indicator based on the first predefined pattern and the second predefined pattern indicating a sanitization status and simultaneously communicate the sanitization status to an authorized user.

11. The system as claimed is claim 10, comprising a mobile device of the authorized person configured to communicate with the lock and fetch the sanitization status of the premises.

12. The system as claimed in claim 11, wherein the mobile device of the authorized person uses a client application to communicate with the lock.

13. The system as claimed in claim 10, wherein the first predefined pattern and the second predefined pattern are configured to enable the sanitization status of the premises only within the predetermined time interval.

14. The system as claimed in claim 10, comprising a sensor configured to sense a level of sanitization inside the premises.

15. The system as claimed in claim 14, wherein the sensor is configured to compare the level of sanitization with a predefined value, wherein the sensor wirelessly communicates the level sanitization to the lock of the premises.

16. The system as claimed in claim 10, wherein the authorized user is a guest, wherein on indication that the sanitization process is completed, the lock is only accessible by the guest and restricted to other authorized users.

17. A computer readable medium comprising a memory storing instructions executed by one or more processors, the one or more processors configured to:

configure a sanitization mode for a predetermined time interval for sanitizing a premises;

receive a first predefined pattern on a lock associated with the premises from a user within the predetermined time interval to indicate starting of the sanitization process by sensing turning of a handle of the lock for a count;

receive a second predefined pattern on the lock within the predetermined time interval to indicate a completion of the sanitization process, by sensing turning of a deadbolt of the lock ON or OFF for a count; and display an indicator based on the first predefined pattern and second predefined pattern indicating a sanitization status and simultaneously communicating the sanitization status to an authorized user.

* * * * *